US007294343B2

(12) United States Patent
Barresi et al.

(10) Patent No.: US 7,294,343 B2
(45) Date of Patent: Nov. 13, 2007

(54) BIODEGRADABLE SORBENTS

(75) Inventors: Frank Barresi, Coralville, IA (US); Kara Hulsey, Dewitt, IA (US); J. Steven Taylor, Muscatine, IA (US); Kevin H. Schilling, Muscatine, IA (US)

(73) Assignee: Grain Processing Corporation, Muscatine, IA (US)

( * ) Notice: Subject to any disclaimer, the term of this patent is extended or adjusted under 35 U.S.C. 154(b) by 0 days.

(21) Appl. No.: 10/172,588

(22) Filed: Jun. 14, 2002

(65) Prior Publication Data

US 2003/0020043 A1 Jan. 30, 2003

Related U.S. Application Data

(60) Provisional application No. 60/298,861, filed on Jun. 15, 2001.

(51) Int. Cl.
*A01N 25/34* (2006.01)

(52) U.S. Cl. ........................ 424/408; 424/84; 424/406; 424/439; 424/442

(58) Field of Classification Search ................ 424/405, 424/406, 408, 439–442, 84
See application file for complete search history.

(56) References Cited

U.S. PATENT DOCUMENTS

| | | | | |
|---|---|---|---|---|
| 3,161,497 | A * | 12/1964 | Amburn | 71/2.6 |
| 4,238,484 | A | 12/1980 | Stein et al. | |
| 5,063,232 | A | 11/1991 | Leyendecker et al. | |
| 5,290,557 | A | 3/1994 | Mason et al. | |
| 5,364,618 | A * | 11/1994 | Meer et al. | 424/84 |
| 5,437,870 | A | 8/1995 | Puritch et al. | |
| 5,571,522 | A | 11/1996 | Munson et al. | |
| 5,607,684 | A | 3/1997 | Lew et al. | |
| 5,609,880 | A | 3/1997 | Munson et al. | |
| 5,639,319 | A | 6/1997 | Daly | |
| 5,658,954 | A | 8/1997 | Targosz | |
| 5,662,958 | A * | 9/1997 | Kennelly et al. | 426/630 |
| 5,690,951 | A | 11/1997 | Lew et al. | |
| 5,939,061 | A | 8/1999 | Vail et al. | |
| 5,968,540 | A | 10/1999 | Brenner et al. | |
| 6,001,382 | A | 12/1999 | Levy | |
| 6,174,538 | B1 | 1/2001 | Branly et al. | |
| 6,187,326 | B1 | 2/2001 | Yamashita | |
| 6,216,634 | B1 | 4/2001 | Kent et al. | |
| 6,368,588 | B1 | 4/2002 | Faehl et al. | |
| 6,384,082 | B1 | 5/2002 | Wirth et al. | |
| 6,391,328 | B1 | 5/2002 | Levy | |
| 6,524,600 | B2 | 2/2003 | Yamashita | |
| 6,602,804 | B2 | 8/2003 | Allen et al. | |
| 2001/0000325 | A1 | 4/2001 | Yamashita et al. | |
| 2001/0047769 | A1 | 12/2001 | McPherson et al. | |
| 2003/0020043 | A1 | 1/2003 | Barresi et al. | |

FOREIGN PATENT DOCUMENTS

| | | |
|---|---|---|
| DE | 195 09 936 C1 | 3/1985 |
| EP | 0115664 | 8/1984 |
| EP | 0 235 530 | 1/1987 |
| EP | 0340948 | 11/1989 |
| EP | 0384251 | 8/1990 |
| EP | 0469690 | 2/1992 |
| EP | 0598746 | 9/1996 |
| EP | 0725562 | 8/1998 |
| EP | 1052899 | 4/2002 |
| EP | 1107666 | 11/2002 |
| GB | 2 206 474 A | 1/1989 |
| JP | 61106505 | 5/1986 |
| JP | 2002087914 | 3/2002 |
| SU | 67694 | 12/1946 |
| WO | WO 01/32013 * | 5/2001 |

OTHER PUBLICATIONS

AMPOFO-Biocontrol Sci. Technol., vol. 5m #4, pp. 417-423—1995□□ □□use of raw materials for production of *Bacillus sphaaericus* insecticide in Ghana.*
Tsao- et al Abst, pap. am.chem. soc. 206 Meet, Pt. 1, AGRO49, 1993□□□□crpou iqc abstract # 1993-86227.*
Abstract: Use of Local Raw Materials—'95 AMPOFO: Biocontrol Sci Technol. vol. 5 #4-417-423.*
Database WPI, Section Ch, Week 199247, Derwent Publications Ltd., London, GB; Class C04, AN 1992-386284 XP002234769 & JP 04 285088 A (Asahi Kogyo Co Ltd), Oct. 9, 1992 (abstract.)
Database WPI, Section Ch, Week 199247, Derwent Publications Ltd., London, GB; Class C04, AN 1992-386265 XP002234770 & JP 04 285089 A (Taki Chem Co Ltd), Oct. 9, 1992 (abstract.)
Database WPI, Section Ch, Week 199518, Derwent Publications Ltd., London, GB; Class D23, AN 1995-136099 XP002234771 & JP 07 060115 A (Hohnen Corp), Mar. 7, 1995 (abstract.)
*Derwent World Patents Index*, WPI Accession No. 2002-457728 (Derwent Week 200249), JP 2002087914 A (Osaka Seiyaku KK) (Sep. 12, 2000)).
*Derwent World Patents Index*, WPI Accession No. 2003-186870 (Derwent Week 200319), JP 2002104253 (Iseki Agric Mach Mfg Co Ltd) (Sep. 27, 2000).
Otsuka Pharmaceut Co Ltd, Insecticide Against Larva of Mosquito, Sonoda Akio, Ao1N 25/12 Abstract (1982).
Kampen, Willem H. et al, Abstract: "Value-added Products from Stillage of Ethanol-from-molasses and Corn-to-ethanol plants", Publication of Technical Papers and Proceedings of the Annual Meeting of Sugar Industry Technologists (1999), Baton Rouge, LA.
Kepner, R. L. et al., Abstract: "Development of a toxic bait for control of mole crickets", Journal of Economic Entomology, Gainesville, FL 1987.
McDaniel, E.I., Abstract: "The Control of certain household pets with poison bran bait", Mich. Agr. Expt. Sta., Quart. Bull. 1934.

* cited by examiner

*Primary Examiner*—Neil S. Levy
(74) *Attorney, Agent, or Firm*—Banner & Witcoff, Ltd.

(57) ABSTRACT

Disclosed is a sorbent that includes spent grain germ, seed meal, or a mixture thereof. The sorbent may be used to introduce a material into an environment. For instance, the sorbent may be used to introduce a control agent, such as an insecticide or larvicide, into an environment. The sorbent also may be used to remove an unwanted material from an environment. For instance, the sorbent may be used to sorb oil or a hazardous chemical that has been spilled. The disclosed sorbents are biodegradable over a wide range of environmental conditions.

5 Claims, No Drawings

BIODEGRADABLE SORBENTS

CROSS-REFERENCE TO RELATED PATENT APPLICATION

This application claims priority to prior application Ser. No. 60/298,861, filed Jun. 15, 2001. The content of this application is incorporated by reference in its entirety.

FIELD OF THE INVENTION

The invention relates to a grain based material useful as a general sorbent. In some embodiments, the invention relates to the introduction of a material into an environment, the material being sorbed within the sorbent. These embodiments are particularly applicable to the introduction of a control agent, such as a mosquito larvicide, into an environment. In other embodiments, the invention relates to the removal of a material from an environment by sorbing the material within the sorbent.

BACKGROUND OF THE INVENTION

Many methods exist for removing an undesired material from an environment. For instance, numerous products are available commercially for removing spilled liquids from a surface. Some such products are used to remove oil from open water, such as when an oil spill has occurred. In this application, it is desirable to selectively remove oil from water. For such absorbents, efforts are sometimes made to increase the selectivity of oil over water.

Currently available products for spill control include clay, kaolin, illite, bentonite, diatomite, hectorite, montmorillonite, attapulgite, silica, silica sand, polypropylene, sodium polyacrylate/polyacrylamides, vermiculite, gypsum, limestone, metal oxides, asphalt, fiberglass, diatomaceous earth, perlite and other materials. Such materials, while satisfactory in function, suffer from certain drawbacks. Many such products contain silica, which poses a hazard to humans. In addition, most such materials are not biodegradable, which is a factor that can limit the options for disposal of the used sorbent material.

There are also several organic spill control products described in the art. Examples of such materials include natural fibers such as grass, pre-cooked cereal kernels, sawdust, cellulose, and peat. U.S. Pat. No. 5,492,881 purports to describe a cellulose based sorbent system, where the cellulose has been treated with an additive to render it both hydrophobic and oleophilic so it will selectively remove oil from water. U.S. Pat. No. 4,969,774 purports to describe the use of pre-cooked and puffed cereals for oil removal. Another document, U.S. Pat. No. 5,399,350, purports to disclose a particulate milled seed material in which the lipids have been removed through solvent extraction and wherein the material is designed to remove and disperse oil from open water and solid surfaces. The composition is a solvent-extracted proteinaceous material derived from grain products having oil sorptive properties. Also, U.S. Pat. No. 5,492,881 purports to describe the use of diatomaceous earth, clay, silica, corncob, peatmoss, perlite, polypropylene, sawdust, cellulose, polystyrene, vermiculite, peat and cork to absorb liquids. This composition is taught as a general absorbent; in this document, it is stated that materials that absorb both water and oil are undesirable. U.S. Pat. No. 5,891,937 purports to disclose the use of corn stalks, husks, cobs, and kernels as carriers. U.S. Pat. No. 6,110,323 purports to disclose the use of delignified waste from hulls, straw, stover, and shells as a carrier. Other carriers are purportedly disclosed in U.S. Pat. Nos. 6,383,609 and 6,391,120. Generally, other biodegradable materials such as peat moss, sawdust, hair, feathers, cotton, cork, starch, bagasse, seeds, seed hulls, and other seed components have also been proposed.

Many methods for introducing a material into an environment also are known. In many cases, it is desired to introduce the material in a delayed-release manner, by which is contemplated that at least some of the material is bound up with another material or otherwise is not immediately available to function in the environment for its intended purpose. For instance, it is often desired to introduce a control agent, i.e., a material that limits the growth or spread of a living thing, into an environment. Known control agents, such as insecticides, larvicides, rodenticides, fungicides, and so forth may be oil-based or water-based. It is desirable to provide a sorbent for such control agents, and in particular, it is desirable to provide a sorbent that allows delayed release of at least some control agents into an environment. Further, it is highly desirable to provide a sorbent that is useful in sorbing both oil- and water-based control agents.

Typical control agents are provided in liquid or solid form. There are advantages and disadvantages to each product form. Liquid pesticides can be applied as a spray, which is advantages in some respect. Drift control of the spray can be a challenge, however, especially in an aerial broadcast application. Solid pesticide products are better at targeting an area for pest control, because there is less drift of the solid product. Pelleted or compacted compositions are typically used in solid pesticide products. The majority of such composition is composed of a carrier or absorbent material, and the active ingredient is usually a small percentage (<10%) of the pellet weight. Another advantage of a solid control agent composition is that the weight of the composition allows penetration into vegetative areas that are less accessible via a liquid spray. Heavier pellets often can penetrate through a tree canopy, whereas liquid droplets would tend to coat and contaminate the tree canopy.

One drawback to many known solid pesticides products is that non-biodegradable carriers often are used in such products. These carriers can lead to contamination of the area of treatment. In recognition of this problem, numerous biodegradable carriers have been provided; examples include materials such as corncob, peanut hulls, and starches. Many known biodegradable carriers are unsatisfactory. In many cases, the resulting composition does not perform as well as a non-biodegradable product. In addition, many biodegradable materials such as corncob, peanut hulls, and starches do not disperse easily when in contact with water, leaving a contaminant residue. Corncob is especially poor in this regard, because it has low density as well as poor dispersibility in water. In addition, when a granular pesticide does not readily disintegrate in an aquatic environment, the active ingredient is not readily released and thus a less efficacious pest control product with residual contaminant pesticide activity is provided.

In the case of mosquito larvicides, such materials ordinarily are released into standing or slowly moving water to destroy larvae growing in the water. It is particularly preferred that the carrier should release at least a portion of the larvicide within the topmost two feet of water in a standing or slowly moving water column, where most or all of the larvae are found. It is further preferred that the larvae in the water column be destroyed within 24 hours, and preferably within 8 hours of treatment. Although the prior art has provided numerous carriers for control agents, not all carriers allow for the preparation of a control agent composition that meets these preferred criteria.

In a first preferred embodiment of the invention, it is a general object to provide a sorbent that is useful in conjunction with the introduction of a material into an environment. In a second preferred embodiment of the invention, it is a general object to provide a sorbent that is useful in conjunction with the removal of a material from an environment, the material being removed by sorption of the material into the sorbent and removal of the sorbed composition thus formed from the environment.

THE INVENTION

The invention provides a number of embodiments in which the sorbing properties of spent grain germ and seed meal are utilized. These organic, naturally derived sorbents, alone or in combination, can be used to introduce material into an environment, or to remove material from an environment. When such sorbent is used to introduce a material into an environment, the environment preferably is one in which the sorbent will biodegrade. In such instances, delayed release of the sorbed material into the environment often is possible. When the sorbent is used to remove material from an environment, the sorbed material composition can be allowed to biodegrade prior to ultimate disposal of the composition. Many of the disclosures in the prior art fail to address the fate of the sorbed composition formed upon removing a material from an environment. Generally, the volume of sorbent introduced into the environment is much greater than the volume of the liquid to be removed from the environment. Where the removed material is or contains a hazardous compound, the relatively large quantity of sorbent having the material sorbed therewithin must also be treated as a hazardous material, which can increase the ultimate disposal cost considerably. The sorbents useful in conjunction with the present invention can be biodegraded, thereby reducing the total volume of material that must be treated as hazardous.

In accordance with one embodiment of the invention, a control agent composition is provided. The composition includes a sorbent, the sorbent being selected from the group consisting of spent grain germ, seed meal, and mixtures thereof, and a control agent sorbed within the sorbent. Most preferably, the composition is in the form of discrete plural pellets, by which is contemplated the product of a pelletizing operation in a pellet mill.

In accordance with another embodiment of the invention, a method for limiting the growth of an undesired pest in an environment is provided. The method includes selecting a control agent for the pest, and introducing into the environment an amount of a control agent composition effective to limit the growth of the pest. The control agent composition includes a sorbent and control agent as described hereinabove.

In accordance with another embodiment of the invention, a method for introducing a material into an environment is provided. A material for which delayed release into the environment is desirable is selected. Subsequently, a granular material composition that includes the selected material sorbed within a sorbent, the sorbent being spent grain germ, seed meal, or a mixture thereof, is introduced into the environment. The timing of the release of the material into the environment can be controlled to an extent by adjusting the integrity of the granules, whereby more durable granules generally will release the sorbed material more slowly than less durable granules.

In accordance with another embodiment of the invention, a method for removing an unwanted material present in an environment is provided. The method includes selecting a sorbent for the material, introducing into the environment an amount of the sorbent effective to sorb at least a portion of the material, allowing at least some of the material to become sorbed to thereby formed a sorbed composition, and removing at least a portion of the sorbed composition from the environment. The sorbed material may be a combustible material, and, in accordance with one embodiment of the invention, a method for generating heat is provided, the method including providing a combustible material composition and oxidizing the combustible material composition. The combustible material composition includes a sorbent and a combustible material sorbed within the sorbent. Preferably, the combustible material is present in an amount of at least 5% by weight of the composition.

DETAILED DESCRIPTION OF THE PREFERRED EMBODIMENTS

The invention contemplates the use of a sorbent, by which is contemplated a material that absorbs and/or adsorbs another material. Generally, absorption is a term used in the art to refer to the penetration of one substance into the inner structure of another substance, whereas the term adsorption refer to adherence of atoms, ions, or molecules onto the surface of another material. It is believed that one or both phenomena occur in accordance with the various embodiments of the invention, but it is contemplated that the material may serve as a sorbent even if only one of the two phenomena is present. By "sorbed within" is herein contemplated the sorption of a material in or on the sorbent.

The sorbent used in conjunction with the invention preferably is spent germ, which is a germ from which oil has been expelled, for instance, by pressing or extraction with an extracting liquid such as hexane or water. Spent grain germ material has numerous advantages, in that it is derived from natural, renewable resources, is biodegradable and safely incinerable, is nontoxic and safe for the environment, and is economical to produce and use. This material is able to sorb both hydrophilic and lipophilic liquids. The spent germ may be washed to render it substantially free of odor components. It is known that washing of the germ will remove substantially odor and flavor components, which may be an advantage in some instances. In other embodiments, unwashed germ may be used. Germ obtained from any suitable grain may be employed in conjunction with the invention. Grains such as corn, wheat, soy, sorghum, barley, and the like are particularly suitable for use in conjunction with the invention. The preferred sorbent is expeller-extruded corn germ. Virgin germ (i.e., germ from which oil has not been extracted) may also be used, whereby in the manufacture of the sorbent as described herein some or all oil present in the germ is extracted.

Alternatively, or in addition thereto, the sorbent used in conjunction with the invention may be a seed meal. Examples of such meals include linseed meal, soybean meal, sunflower meal, cottonseed meal, rapeseed meal, peanut meal, safflower seed meal, and combinations thereof. By "seed" is meant to include that part of a plant which is capable of forming a new plant upon germination, e.g., whole grains of wheat, including the fruit or fruit-like structure housing the seed. The seed meal comprises a spent oil bearing seed residue, which is a seed residue from which oil has been expelled, such as by solvent extraction or expeller extraction. The extracted residue then is ground, by which is contemplated the reduction of the residue to smaller particles, preferably to a semi-course to fine powder. It is contemplated that some seeds will include a hull that may (but need not) be removed prior to expelling oil and grinding. Thus, the meal may comprise a dehulled meal. The seed meal in some embodiments is washed to substantially remove odor components therefrom.

The germ and seed meal component of the sorbent collectively should be present in the sorbent in an amount of at least 50% by dry basis weight of the sorbent. Preferably, the germ and meal are present in a greater amount, such as an amount of 60%, 70%, 80% or 90% by weight of the sorbent. Most preferably, the germ and meal collectively are present in an amount of 100% by dry basis weight of the sorbent, that is, the sorbent includes the meal and/or germ to the substantially or complete exclusion of other sorbents. With respect to one another, the germ and meal can be used in any ratio desired. For instance, expresses as a percentage, the ratio may be 100% meal, 90% meal, 80% meal, 70% meal, 60% meal, 50% meal, 40% meal, 30% meal, 20% meal, 10% meal, or 0% meal (i.e., 100% germ). Other sorbents, such as these described in U.S. Pat. No. 6,391,328, optionally may be used in conjunction with the sorbents described herein, but preferably, such other sorbents are not present.

The sorbent may be used in conjunction with the introduction of a material into an environment. The environment can be any place, area, or region in which the introduction of the material is desired. Generally, the material is selected as being desirable for use in the environment. For instance, the material may be a control agent, by which is completed a material that limits the growth of unwanted pests in the environment. A control agent preferably is selected as being an agent that limits the growth of the pest, by which is contemplated checking the spread of the pest by killing, sterilizing, destroying eggs or otherwise limiting the growth of the pest. Control agents generally are toxic chemicals; in accordance with the invention, any control agent now known or otherwise found to be suitable for use in limiting the growth of a pest may be used. The pest may be present in the environment, or may not be present in the environment (in other words, it is contemplated that the environment may be treated prophylactically). The pest can be any organism whose presence in the environment is undesired. Any organism found in the Animalia, Protista, Fungi (in particular non-mold fungi), Plantae, or Monera kingdoms may be deemed a pest in particular circumstances, and the control agent may be any agent that limits the growth of such pest in the environment. With respect to animals, the pest may be mammal, for instance, a rodent such as a mouse or rat, or a non-mammal, such as a fish, bird or other animal. The invention is believed to be particularly applicable to the control of animals in the phylum Arthropoda, including especially the classes Insecta (representing insects, millipedes, and centipedes), and Cheliceramorpha, especially arachnids. The control agent in preferred embodiments may be a rodenticide, a herbicide, an insecticide, a fungicide, or a bactericide. Specific embodiments of the invention employ, for instance, a larvicide, a pupicide, an ovicide, a hormone, a growth regulator (e.g. an insect growth regulator), a biological control agent, a microbial control agent, a toxicant, a fumigant, a pheromone, a repellent, a chemosterilant, a miticide, an acarcide, a molluscicide, an avicide, a predicide, an algaecide, a nematicide, an amoebicide, a nymphicide, and the like. In preferred embodiments, the control agent is selected from among an animal control agent (which may be a control agent for any species in the kingdom Animalia), a plant control agent (any species which may be a control agent for any species in the kingdom Plantae), a non-mold fungal control agent (which may be a control agent for any species in the kingdom Fungi, excepting the molds), a protist control agent (which may be a control agent for any species in the kingdom Protista) or a monera control agent (which may be a bacterial species or any other species in the Monera kingdom). In some embodiments, the control agent may be a virus control agent. Two or more agents can be combined to increase efficacy or to achieve multifunctional performance in the same composition.

Specific preferred examples of suitable control agents include insecticides such as temephos, chlorpyfifos, methyl isocyanate, methoprene, propaphos, DURSBAN® dimilin, malathien, carbaryl, and diazinon; herbicides such as 2,4-D and 2,4-D ester, ammonium sulfamate, BROMACIL®, copper salts, molinate, propanil, pyrazolate, metolachlor, and the like. Other control agents include bioactives such as *Bacillus thuringiensis* and *Bacillus sphaericus*; flugicides, such as fenoxanil, iprobenfos, menopril, tricyclozole, and valdamycin, and the like. The invention is not limited to the foregoing, and indeed any material that functions as a control agent may be used in conjunction with the invention. U.S. Pat. Nos. 4,911,952; 4,983,390; 5997,445; 6,159,489; 6,316,447; 6,335,027; and 6,340,656, all disclose numerous control agents, any or all which in certain embodiments may be deemed suitable for use in conjunction with the invention.

The control agent or other material sorbed within the sorbent may be a lipophilic or oleogenous material, or may be a hydrophilic material or a combination thereof (such as an emulsion). The material may be present in any amount with respect to the sorbent suitable for the intended purpose of the sorbent/material composition. In some embodiments, the material is present in an amount of at least 5% by weight of the total composition, more preferably at least 7% by weight, and even more preferably, at 10% by weight. When the sorbed material is a control agent, the sorbed material preferably is present in an amount ranging from 0.001 to 50% by weight, more preferably, from 0.001 to 10% by weight, and even more preferably, from 0.005 to 5% by weight of the composition. In some embodiments, the sorbed material is present in an amount from 0.05 to 1%, or, within this range, from 0.05 to 0.5% by weight. More generally, any amount suitable for the intended purpose may be employed in conjunction with the invention. The composition optionally may include any other additives, which may be present in any amounts suitable for their intended purposes or omitted altogether. Examples of such additives include surfactants, spreading agents, adjuvants, other carriers, binders, deflocculating agents, dispersing agents, synergists, penetrants, suspending agents, baits, phagostimulants, sticking agents, stabilizers, coupling agents, foaming or antifoaming agents, diluents, waxes, oils, superabsorbents, and more generally, any other additives.

The sorbents described herein are not limited to the introduction of a control agent into an environment. To the contrary, the sorbets can be used to introduce any desirable sorbable materials into an environment. It is contemplated that in some cases the sorbable material may be a solid material that is carried in or on the sorbent. In one embodiment of the invention, the sorbable material is a fertilizer. Any suitable material or synthetic fertilizer may be employed in conjunction with the invention. In one embodiment, the sorbable material is an animal nutrient, such a vitamin or mineral. These materials may be present in any amounts suitable for their intended purpose. The selection of specific ingredients, loading levels, and application rates may be made by one is skilled in the art. One embodiment of the invention encompasses a method for fertilizing an arable area by applying a fertilizer composition as described above. In another embodiment, the invention encompasses a method for providing nutrients to an animal, the method including feeding the animal an animal nutrient composition as described above. The animal may be for instance, a horse, a cow, a pig, a sheep, a bird, or even a human.

The composition that includes the sorbent and sorbed material (including any additives) may be provided in any suitable form. Most preferably, the composition is provided in the form of discrete plural particles of a substantially uniform and homogenous admixture of the sorbent and the sorbed materials. In accordance with a preferred embodiment of the invention, the particles are in a form of compressed or compacted particles, i.e., in the form of granules. By "granules" is meant particles that are compressed or compacted, such by a pelletizing, extrusion or similar compacting step. Such compression or compacting of the particles is preferred, inasmuch as the intraparticle cohesion of the particles will be enhanced by such compacting or compressing step.

The granules may be prepared via any suitable manner. Preferably, the material to be sorbed, if not a liquid, is dissolved or suspended in a liquid and the liquid is applied to the sorbent, followed by compression of the mixture to form granules. In a highly preferred embodiment of the invention, the granules are prepared by pelletizing the sorbent in a pellet mill. The composition may be prepared by sorbing the material into pellets thus formed, or alternatively may be prepared by pelletizing a mixture of the material and the sorbent. In either case, the pellets exiting the pellet mill may be ground or crumbled to thereby reduce the granules of the composition to a desired granule size. The mixture may be pelletized under any suitable conditions. Typically, the ingredients are pre-ground and are introduced into the pellet mill with moisture. Typical moisture content ranges from 2-30%, more preferably 5-15% by total weight of the blend. The blend is pelleted through a die such as a $\frac{3}{32}$ in×2 in die at any suitable temperature, preferably a temperature ranging from 150° F. to 220° F., more preferably from 180° F. to 200° F. Final moisture preferably is in the range from 4-20%, more preferably from 7-12% by total weight.

After pelleting, the pellets may be cooled and crumbled through dry rollers to reduce the size of the granules (it is also possible to cut the pellets from the die). The final granule size may vary depending on the application. For an application such as mosquito control, the granule size preferably should be between 4 and 30 mesh (U.S. standard test sieve. ASTM E-11 specification) and more preferably should be between 6 and 20 mesh. Fines generated during the pelletizing process may be removed by screening, preferable on a 10-mesh screen to a level of less than 20% by weight and ideally less than 5%. Such fines may be recycled.

In the pelletizing operation, use of a lubricity agent such as corn oil may be necessary or helpful. Other lubricants such as added corn oil or oils from soy, peanut, sunflower, rapeseed, canola, coconut, or cotton, or animal fats such as tallow, yellow grease, or white grease, may be used. Other lubricants include lecithin, waxes, fish oils, castor oil, long-chain alkyl sulphonates, alkyl poyglucosides, tall oil, stearates, and silicones. The lubricant (including any oil present in the germ) preferably is present in an amount of up to 30% by total weight of the composition (excluding moisture) more preferably, an amount of 10-15% by weight. Pelletizing is not the only manner of forming suitable granules. For instance, in another embodiment of the invention, extrusion of sorbent through a dye and grinding of the extrudate to a suitable granular size is useful in conjunction with the preparation of the composition. Once again, the extrudate may itself comprise a composition of a sorbent and the material to be sorbed, or the material may be sorbed within granules of extruded sorbent subsequent to extrusion.

The granules should be sufficiently cohesive for use for their intended purpose. Especially when the granule is used as a carrier for control agent, the granule must have sufficient integrity to survive the production, transport, and application of the product. If the granule is too durable, however, it will not disintegrate easily, and may not be effective in releasing the control agent in the desired manner, for instance, when the granule is introduced into a water column. In embodiments of the invention where a delayed release of the control agent or other sorbed material is desired, the granules may be made more durable by incorporating additional binder or cohesiveness agent. The binder may comprise an extrudate of corn hulls and sodium hydroxide (as taught is copending application Ser. No. 09/901,342, filed Jul. 9, 2001), lignin, lignosulfate, hemicelluloses, celluloses, water, starch hydrolyzates, hydrogenated starch hydrolyzates, fatty acids, and clay materials such as bentonite and zeolites. In such embodiments, the binder preferably is present in an amount of about 5% by weight of the granule. In some embodiments of the invention, the granules may include a polysaccharide cohesiveness agent to enhance the cohesiveness of the granules. The cohesiveness agent is believed to provide additional hydroxyl groups, which groups enhance the bonding between grain proteins within the sorbent granules. It is further believed that the additional hydroxyl groups so function by enhancing the hydrogen bonding of proteins to starch and to other proteins. When used, the polysaccharide cohesiveness agent may be present in any amount suitable to enhance the cohesiveness of the sorbent granules. Generally, the cohesiveness agent may be present in a dry basis amount ranging up to about 45% by weight of the sorbent granules, preferably, an amount ranging from about 3% to about 35% by weight, more preferably, an amount ranging from about 5% to about 25% by weight. When the binder is or includes virgin germ, some or all of this may come from starch naturally present in the virgin germ In accordance with these embodiments of the invention, any suitable polysaccharide may be used in conjunction with the invention, and thus, for example, the cohesiveness agent may comprise one or more polysaccharides such as dextrin, maltodextrins, starches, flours, cellulosics, hemicellulosics, and the like. Preferably, the cohesiveness agent comprises a starch, and most preferably, the cohesiveness agent comprises a corn starch.

When a polysaccharide cohesiveness agent is used, preferably a supplemental cohesiveness agent also is used. In accordance with the invention, the supplemental cohesiveness agent is an ionic species that is believed to enhance protein-protein and/or protein-starch interactions. Any suitable ionic salt may be used in conjunction with the invention. For example, in accordance with preferred embodiments of the invention, the supplemental cohesiveness agent is selected from among the alkali and alkaline-earth salts of common anions, such as the halide, nitrate, nitrite, carbonate, phosphate, sulfate, and bicarbonate salts, and the like. More preferably, the supplemental cohesiveness agent is selected from the group consisting of sodium chloride, calcium chloride, sodium carbonate, calcium carbonate, sodium bicarbonate and mixtures thereof. Even more preferably, the supplemental cohesiveness agent is selected from among sodium chloride, calcium carbonate, and mixtures thereof. Most preferably, the supplemental cohesiveness agent is sodium chloride. The supplemental cohesiveness agent may be present in any amount sufficient to assist the cohesiveness agent in enhancing the cohesion of the granules. When used, the supplemental cohesiveness agent preferably is present in an amount of at least about 0.05% by dry basis weight, of the composition exclusive of the polysaccharide cohesiveness agent. More preferably, the supplemental cohesiveness agent is present in an amount ranging from about 0.05% to about 10% by weight; more preferably, about 0.1% to about 8% by weight; and most preferably, about 1.5% to about 4% by weight. In a particularly preferred embodiment, the supplemental cohesiveness agent is present in an amount of about 2% by weight of the composition.

To prevent or inhibit spoilage, the sorbent composition may include a preservative. Preferably, the sorbent composition includes a mold inhibitor, which may be present in any amount sufficient to inhibit the molding of the sorbent composition. Any suitable mold inhibitor may be employed in conjunction with the invention. The mold inhibitor preferably is selected from among the propionate salts, and most preferably is selected from the group consisting of sodium propionate and calcium propionate. Other preservatives include sodium metabisulfite, citric acid, vitamin C, vitamin E, butylated hydroyxytoluene (BHT) butylated hydroxyanisole (BHA), and sodium benzoate. When a mold inhibitor is employed, it preferably is present in an amount ranging from about 0.02% to about 3.5% by weight. The mold inhibitor may function to some extent as agent for controlling mold if the composition is introduced into an environment; however, at the levels used herein, the mold inhibitor is intended for the purpose of retarding mold of the sorbent composition itself.

The composition may be introduced into an environment via any suitable means. Where it is desired to disseminate the composition over a large area, the composition may be disseminated from an aircraft, such as plane, helicopter, blimp, balloon, or the like, or may be disseminated from a watercraft. Particularly when the control agent is a mosquito adulticide or larvicide, the environment may be a water-containing environment, by which is contemplated any environment containing standing or slowly moving water. For example, the water-containing environment may be a pond, lake, swamp, marsh, bog, area with collected rainwater, (such as a tire) and so forth. It is contemplated that in these or other embodiments of the invention the environment may be an indoor environment. The composition preferably is formulated to release at least a portion of the larvicide within the first two feet of water column.

The sorbent composition also may be used to remove a material from an environment. In accordance with this embodiment of the invention, at least a portion of undesired material present in an environment may be removed by introducing a sorbent into the environment, allowing the sorbent to sorb at least a portion of the material, and removing at least a portion of the sorbed composition from the environment. The material which may be removed from the environment is not limited to the materials described herein, but to the contrary it is contemplated that any materials that is sorbable by the sorbent composition may be removed form an environment. For instance, the material may be an oleogenus or lipophilic material, or may be a hydrophilic material. In some embodiments, the material may be a gaseous material, such as ammonia. Generally, the sorbent may be prepared as described hereinabove, and may be introduced into the environment in any suitable manner, for instance, by dispersing the sorbent from an aircraft or watercraft as described above. The sorbent may be introduced into the environment in any amount effective for its intended purpose.

The sorbent used in conjunction with the invention is incinerable. It is contemplated that the sorbed material may be a combustible material, and in particular a hydrophilic material such as ethanol or an oleogenous material such as oil. It is contemplated that a combustible material composition so composed may be oxidized, such as by incineration, to thereby generate heat. The heat thus generated may be used in industrial applications or may be used to generate electrical energy. The combustible material composition may include any suitable ratio of sorbent to combustible material. Preferably, the composition includes from 1-75%, by weight combustible material, more preferably, the combustible material is present in an amount of at least 5% by weight, even more preferably, the combustible material is present in an mount from 10-75% by weight.

The sorbents useful in conjunction with the invention are biodegradable at 25° C. By "biodegradable" is contemplated that the sorbents are susceptible to degradation via microbial influence or other breakdown of the biological structure of the sorbent, such as by thermal or internal chemical or biochemical influence. It is further contemplated that the sorbent will be biodegradable over a wide range of other temperatures. When the sorbent is used to introduce a material into an environment, in particular an outdoor environment, the sorbent preferably is biodegradable in the environment. Such biodegradability prevents long-term contamination of the environment of the sorbent, and, in some embodiments, may effect a delayed release of the sorbed material into the environment. In embodiments of the invention where the sorbent is used to remove material from an environment, the sorbent may be allowed to biodegrade after removal of the sorbed unwanted material but before final disposal of the sorbed material compositions. The biodegradation of the sorbent will in some instances reduce the volume of the sorbed material composition, thereby reducing the disposal costs (particularly in the case of a hazardous material). The sorbed material may be stored until the volume of the material has been reduced by a desired amount preferably at least 10%, more preferably 15%, and even more preferably 20% of the original volume.

The following Examples illustrate the invention, but should not be construed as limiting the invention in scope.

EXAMPLE 1

Experiments were carried out to evaluate the ability of spent corn germ to sorb various liquids. For each liquid evaluated, 15 grams of sorbent was mixed with 10-50 grams of the liquid to be tested. After 2 hours, the liquid not sorbed by the germ was drained off, and the quantity of liquid retained by the sorbent was determined. Four commercial products were also evaluated, two of which were claimed to be both oil and water absorbents. The products picked up from 20 to 25% of their weight of water in the same period of time. The oil absorptive capacities of the germ and the commercial products are similar.

Data below is expressed for each product as % of its weight in liquid absorbed.

|  | Germ | Product A | Product B | Product C |
|---|---|---|---|---|
| Water | 600 (after 2 hours) | 26 | 42 | 32 |
| Ethanol | 72 | 74 | 74 | 70 |
| Mineral oil | 58 | 40 | 36 | 48 |
| Diesel fuel | 28 | 22 | 20 | 32 |

Product A is a silica-based commercial product.
Product B is a silica/clay-based commercial product.
Product C is a silica-based commercial product.

As seen, the germ was superior to the commercial products. The germ was found to sorb at least 300% of its weight of water within 5 minutes, although it is believed that the ultimate capacity is even greater over time.

EXAMPLE 2

This example demonstrates the sorption of gaseous ammonia by spent corn germ.

Sorption isotherms were conducted by treating air that contained 200 ppm $NH_3$ with different levels of ground spent corn germ. Air test chambers each having a volume of 3717.4 $cm^3$ were each prepared to contain a standard mass of gaseous ammonia by placing into each chamber an open top plastic weigh boat containing 10.00 mL of a standard ammonia solution made to contain 0.000259 g $NH_3$ per mL. Each test chamber contained a total of 0.00259 g $NH_3$, which at equilibrium would exist both as a free gas and as gas dissolved in water. Directly preceding the addition of the ammonia solutions to the test chambers, different masses of ground spent germ of 100 g, 10 g, and 1.0 g had been added to three different test chambers. Two additional test chambers were not provided with grain germ but had only the weigh boats containing the ammonia solution. After equilibration at 20° C. for 23 hours, the concentrations of gaseous ammonia in the test chambers were measured with Draeger Tubes.

The relationship between ppm and $mg/m^3$ was calculated according to the following equation:

$$\text{ppm} = \text{molar volume} \times (mg/m^3) \div \text{molar mass}$$

wherein molar volume is 24.1 liters, and molar mass is 17.0 grams.

Using this calculation, a concentration of 200 ppm $NH_3$ represents 20.23% of the total $NH_3$ added.

The two test chambers to which no spent germ had been added were each found to contain 200 ppm $NH_3$. Surprisingly, even the smallest amount of germ added to the chamber was sufficient to sorb gaseous ammonia to a level below the level of detection. The three test chambers to which the three different amounts of ground spent germ had been added were each found to contain 0 ppm $NH_3$.

EXAMPLE 3

Preparation of Germ for Insecticide Usage

Unwashed spent corn germ (Grain Processing Corporation, 25 pounds (10% moisture) was fed into a California Pellet Mill. The conditioner temperature on the mill was 44° C. and a pellet die with 0.125×1.25 inch openings was used. The pelleting temperature was 67-68° C. The pelletized product was crumbled and screened across a 20-mesh screen to remove fines. The resulting product moisture was 11.5%.

EXAMPLE 4

Pelletized Germ as a Mosquito Larvicide Carrier

The pelletized germ of Example 3, 10 pounds, is imbibed with 0.2 pounds of Altosid® liquid larvicide (5% active (S)-methoprene). Mixing is carried out so that an even distribution of the larvicide is achieved throughout the pellets. The larvicide containing pellets are then used to treat an open saltwater marsh

EXAMPLE 5

Pelletized Germ as a Mosquito Adulticide Carrier

The pelletized germ of Example 3, 10 pounds, is imbibed with 0.1 pounds of Dursban® 4E liquid insecticide (44.8% active chlorpyrifos). Mixing is carried out so that an even distribution of the insecticide is achieved throughout the pellets. The insecticide containing pellets are then used to treat an open saltwater marsh at an application rate of 0.5 pounds per acre.

EXAMPLE 6

Example 4 is repeated, except that the sorbent includes grain germ, starch, and salt, which are present in a ratio of 78:20:2 with respect to one an other.

EXAMPLE 7

Example 4 is repeated, except the sorbent includes soy meal.

EXAMPLE 8

Example 4 is repeated, except the sorbent includes soy meal, starch, and salt which are present in a ratio in 78:20:2 in respect to one another.

EXAMPLE 9

Example 4 is repeated, except the sorbent includes linseed meal.

EXAMPLE 10

Example 4 is repeated, except the sorbent includes linseed meal, starch, and salt which are present in a ratio 78:20:2 with respect to one another.

EXAMPLE 11

Example 4 is repeated, except that the sorbent is sunflower meal.

EXAMPLE 12

Example 4 is repeated, except that the sorbent is a 50:50 mixture of spent grain germ and sunflower meal.

EXAMPLE 13

Example 4 is repeated, except that the sorbent is a 50:50 mixture of sunflower and linseed meal.

EXAMPLE 14

U.S. Pat. No. 6,098,569 issued Aug. 8, 2002 to Kent et al. is hereby incorporated by reference in its entirety. A sorbent is prepared in accordance with "animal litter" set forth as example 2. The sorbent is used to sorb oil from a cement surface.

EXAMPLES 15-48

Ground germ, virgin germ, hexane extruted germ (HEG), corn hulls, granular starch (B200 and B700, available from Grain Processing Corporation of Muscatine, Iowa), Biobond E310 (a hemicellulose product available from Grain Processing Corporation), MALTRIN® M150 (a maltodextrin available from Grain Processing Corporation), wheat middlings, distearyl dimethyl ammonium chloride (TA-100), carboxymethyl starch extrduate (G120), distillers dried grains (DDG) and liquid feed syrup (LFS) were provided and fashioned into pellets. The moisture content of all of the pellets was from 2%-10%. The fat (corn oil) level of the blends ranged from 6-15%. Protein content was 20-30% of the total blend. The formulations in the following table were prepared (the figures in the following table are expressed as weight ratios).

content of the blend to 7.6%. After fifteen minutes of blending, the ground material was conveyed to a California Pellet Mill. The die size was 3/32"×2". The pellets were cut-off at the die at about ½" in length. The feed screw setting was 8 (~3,000 lbs/hour.). The pelleting temperature was 180° F. and the mill amps were 45. The steam setting to maintain temperature was 63 psi. The overall runnability of the product was excellent and no mill amp surges were observed.

The pellets were conveyed from the pellet die to a cooler to allow the pellets to cool to ambient temperature. Airflow to the cooler was minimized. The pellets were then conveyed to a dual roll crumbler, set to obtain a granule size of 35-75% through an 8-mesh screen. The screening consisted of a 30 seconds to one minute manual shake on an 8 mesh screen, so actual granule of size was smaller than measured by this in process technique. The crumbled pellets were then conveyed over a 10-mesh screen to remove fines. The fines were recycled back to the mill for re-pelleting. The final granules were packaged in 50-pound poly lined bags to prevent moisture loss.

Examples 17, 28, and 29 also were prepared in accordance with the aforementioned procedure, but with different starting blends.

| Weight Ratio | Unwashed germ | Virgin germ | HEG | HULLS | B200 | B700 | E310 | M150 | Wheat Midds | Citric Acid | NA$_2$CO$_3$ | TA100 | DDG | LFS | G120 |
|---|---|---|---|---|---|---|---|---|---|---|---|---|---|---|---|
| Examples: | | | | | | | | | | | | | | | |
| 15 | 100 | | | | | | | | | | | | | | |
| 16 | 100 | | | | | | 3 | | | | | | | | |
| 17 | 100 | | | | | | | | | | | | | | |
| 18 | 100 | | | | | | | | | | | | | | | 1 |
| 19 | 95 | 5 | | | | | | | | | | | | | |
| 20 | 95 | 5 | | | | 5 | | | | | | | | | |
| 21 | 90 | 10 | | | 10 | | | | | | | | | | |
| 22 | 90 | 10 | | | | | | 10 | | | | | | | |
| 23 | 90 | 10 | | | | 20 | | | | | | | | | |
| 24 | 90 | 10 | | | | | | | | | | | 5 | | |
| 25 | 90 | 10 | | | | | 5 | | | | | | | | |
| 26 | 90 | 10 | | | | | | | | 0.1 | 0.2 | | | | |
| 27 | 90 | 10 | | | | | | | | | | | | | |
| 28 | 90 | 10 | 20 | | | | | | | | | | | | |
| 29 | 90 | 10 | | | | | | | | | | | | | |
| 30 | 90 | | | 10 | | | | | | | | | | | |
| 31 | 90 | | 10 | | | 3 | | | | | | | | | |
| 32 | 90 | | | | | | | | | | | 10 | | | |
| 33 | 90 | | | | | | | | | | | | | 10 | |
| 34 | 85 | 15 | | | | | | | | | | | | | |
| 35 | 85 | 15 | | | | 5 | | | | | | | | | |
| 36 | 85 | 15 | | | | | | | | | | | | | |
| 37 | 85 | 15 | | | | | | | | | | | | 10 | |
| 38 | 85 | 15 | | | | | | | | | | | | | 1 |
| 39 | 75 | | 25 | | | | | | | | | | | | |
| 40 | 75 | | | 25 | | 5 | | | | | | | | | |
| 41 | 50 | 50 | | | | | | | | | | | | | |
| 42 | 50 | | | 50 | | 5 | | | | | | | | | |
| 43 | 20 | 10 | | 70 | | | | | | | | | | | |
| 44 | | 10 | 90 | | | | | | | | | | | | |
| 45 | | 10 | 90 | | 10 | | | | | | | | | | |
| 46 | | 10 | | | | | | 90 | | | | | | | |
| 47 | | 100 | | | | | | | | | | | | | |
| 48 | | 90 | | 10 | | | | | | | | | | | |

With reference to Example 36, seventeen hundred pounds of ground, unwashed, expelled germ was blended with 300 pounds of ground virgin germ in a ribbon blender. The starting moisture of the blend was 3.9%. Water, 78 pounds, was added to the ribbon blender to bring the total moisture With reference to Example 32, unwashed, ground, expelled germ, 8.5 pounds, was blended with 1.5 pounds of ground virgin germ and 0.5 pounds of B700 cornstarch. The resulting moisture of the blend was 7.9%. The blend was pelleted through a 3/32×5/8 inch die on a California Pellet Mill. The pellets were cut at the die so that the optimal pellet size could be achieved. The conditioner temperature was 160° F. and this temperature was maintained through the die. The feed setting was 45 and the mill amps were 3.6.

The resulting product moisture was 11.4%.

This procedure was followed for the remainder of the blends of Examples 15-48. (except Examples 17, 28, 29, and 36).

Granule size, durability, water disintegration; and composition were evaluated for several of the foregoing compositions.

A) Granule Size:

Screen profiles were obtained by weighing 100 g of granules and separating the granules on a Tyler Ro-Tap Sieve Shaker. Shaking time was 10 minutes. The screens used were U.S.A. standard sieves 8, 10, 12, 14, 16 and 20 mesh. Any particles that passed through the 20-mesh screen were considered fines. The screen profiles are listed in the following table.

Industries, Edison, N.J.) which is a basket-rack assembly with six open-ended transparent tubes (7.75 cm long, 23 mm wide), of which only two tubes were used at any given time. The tubes are held in place by top and bottom plexiglass plates. The assembly has a woven stainless steel wire mesh (1.8-2.2 mm apertures) attached to the lower plate to allow for water to pass freely in and out of the tubes. The assembly was suspended on a cantilever attached to a motor that consistently raises and lowers the assembly at approximately 30 cycles per minute through a distance of 5.5 cm. A 0.25 g aliquot of >20 mesh granules was placed into the individual tubes (each sample was evaluated in duplicate). The basket-rack assembly was then submerged into a 4L Pyrex No. 1000 beaker containing 3.5 L of 27° C. tap water, and the motor turned on to initiate the movement of the basket. The number of granules remaining in the basket was measured after 5, 10 and 15 minutes and the two values per sample were averaged. The granules disintegrated with time so that the majority of the pellets broke apart and fell through the mesh screen during the test. The following results were obtained.

| Screen Profile: % ON | 8 mesh | 10 mesh | 12 mesh | 14 mesh | 16 mesh | 20 mesh | Pan |
|---|---|---|---|---|---|---|---|
| Example: | | | | | | | |
| 16 | 1.7 | 13.5 | 19.3 | 24.7 | 16.4 | 15.6 | 8.2 |
| 17 | 37.6 | 30.7 | 12.7 | 5.9 | 2.9 | 3.0 | 7.3 |
| 19 | 32.8 | 31.2 | 15.3 | 10.2 | 5.1 | 3.2 | 2.2 |
| 22 | 2.8 | 17.3 | 21.1 | 24.6 | 15.6 | 12.7 | 5.6 |
| 23 | 51.1 | 23.9 | 7.6 | 6.0 | 4.5 | 4.2 | 2.7 |
| 26 | 36.8 | 34.7 | 8.9 | 6.5 | 4.3 | 3.8 | 4.9 |
| 28 | 22.4 | 26.2 | 20.8 | 12.8 | 6.1 | 4.9 | 6.8 |
| 29 | 17.8 | 28.3 | 25.2 | 14.1 | 4.9 | 3.8 | 6.0 |
| 30 | 2.2 | 18.6 | 19.2 | 20.4 | 13.5 | 14.4 | 11.7 |
| 35 | 33.1 | 24.2 | 14.6 | 12.5 | 7.3 | 5.2 | 3.1 |
| 36 | 25.7 | 39.5 | 19.7 | 6.2 | 2.2 | 1.8 | 4.9 |
| 44 | 0.2 | 2.5 | 11.3 | 23.5 | 21.8 | 24.1 | 16.1 |
| 50 | 16.6 | 24.2 | 17.1 | 15.1 | 10.8 | 9.2 | 7.0 |

B) Granule Durability

Granule durability was measured by using a Ro-Tap sieve shaker. A 50-gram aliquot of granules that had been previously screened to remove all fines less than 20 mesh was reapplied on a 20-mesh screen. The granules were then re-shaken on the Ro-Tap for 20 minutes. The fines were measured to give an indication of how easy the granules broke apart. Durability analyses are shown in the following table.

| | Fines | |
|---|---|---|
| Example: | g in Pan | % in Pan |
| 14 | 0.4 | 0.8 |
| 19 | 0.9 | 1.8 |
| 23 | 0.6 | 1.2 |
| 26 | 2.0 | 4.0 |
| 28 | 0.6 | 1.2 |
| 29 | 0.5 | 1.0 |
| 35 | 0.5 | 1.0 |
| 36 | 0.3 | 0.6 |

C) Granule Water Disintegration

The granule water disintegration test is a modification of the U.S. Pharmacopoeia 710 tablet disintegration test. The apparatus used was a VanKel® disintegration tester Vankel

| | # of Pellets | | |
|---|---|---|---|
| Example: | Avg 5 min | Avg 10 min | Avg 15 min |
| 14 | 22 | 12 | 2 |
| 17 | 9 | 1 | 1 |
| 19 | 9 | 3 | 1 |
| 22 | 13 | 8 | 1 |
| 23 | 18 | 9 | 4 |
| 26 | 0 (4 min) | 0 | 0 |
| 28 | 9 | 1 | 0 |
| 29 | 7 | 1 | 1 |
| 30 | 8 | 7 | 4 |
| 35 | 8 | 4 | 2 |
| 36 | 5 | 1 | 0 |
| 44 | 19 | 11 | 7 |
| 45 | 1 | 0 (6 min) | 0 |

D) Granule Chemical Analysis

Selected granule samples were analyzed for moisture (Ohaus moisture balance), fats (ISCO SFE) and proteins (LECO nitrogen analyzer). The following results were obtained.

| Example: | Moisture | Fats | Protein |
|---|---|---|---|
| 17 | 7.4 | 7.2 | 25.2 |
| 19 | 9.0 | 9.8 | 24.4 |
| 23 | 7.0 | NR* | NR |
| 26 | 10.8 | NR | NR |
| 28 | 7.3 | 9.7 | 21.6 |
| 29 | 7.2 | 10.5 | 23.6 |
| 35 | 9.0 | 13.2 | 22.4 |
| 36 | 6.4 | 12.7 | 23.9 |

*Not Recorded

For mosquito control, Example 36 is preferred.

It is thus seen that in various embodiments the foregoing general objects have been satisfied. The invention provides a sorbent which is useful in conjunction with the introduction of a material into an environment, and in conjunction with a removal of a unwanted material from an environment.

All references, including publications, patent applications, and patents, cited herein are hereby incorporated by reference.

The use of terms such as "a" and "an" and "the" and similar referents in the context of describing the invention is to be construed to cover both the singular and the plural, unless other wise indicated herein or clearly contradicted by context. All methods described herein can be preformed in any suitable order unless otherwise indicated herein or otherwise clearly contradicted by context. The use of any and all examples, or exemplary language provided herein, is intended to illuminate the invention and does not pose a limitation on the scope of the invention. No language in the specification should be construed as indicating any non-claimed element as being essential to the practice of the invention. Preferred embodiments of this invention are described herein. Variations of those preferred embodiments may become apparent to those of ordinary skill in the art upon reading the foregoing description. Accordingly, this invention includes all modifications and equivalents of the subject matter recited in the claims appended hereto as permitted by applicable law.

What is claimed is:

1. A composition comprising:

a spent corn germ sorbent; and a first control agent comprising a mosquito larvicide, said first control agent sorbed within said sorbent, said composition being in the form of discrete plural compacted particles, said particles comprising pellets.

2. A composition according to claim 1, said composition further comprising a second control agent.

3. A composition according to claim 1, said larvicide being present in an amount of 0.001 to 50% by weight of said composition.

4. A composition according to claim 3, said larvicide being present in an amount of 0.001 to 10% by weight of said composition.

5. A composition according to claim 3, said composition further comprising a second control agent.

* * * * *